United States Patent [19]

Molter et al.

[11] 4,318,898
[45] Mar. 9, 1982

[54] TECHNETIUM-99M-LABELLED (2,4,5-TRIMETHYLACETANILIDO)-IMINODIACETATE FOR LIVER FUNCTION DIAGNOSIS, CHLOROACETRIC ACID (2,4,5-TRIMETHYLANILIDE), (2,4,5-TRIMETHYLACETANILIDO)-IMINODIACETATE, AND PROCESS FOR THEIR PREPARATION

[75] Inventors: Michael Molter, Frankfurt am Main; Gerhard Kloss, Kelkheim; Eberhard Schickel, Selters, all of Fed. Rep. of Germany

[73] Assignee: Hoechst Aktiengesellschaft, Frankfurt am Main, Fed. Rep. of Germany

[21] Appl. No.: 105,108

[22] Filed: Dec. 19, 1979

[30] Foreign Application Priority Data

Dec. 21, 1978 [DE] Fed. Rep. of Germany ....... 2855334

[51] Int. Cl.$^3$ ............... A61K 49/00; A61K 43/00; G01T 1/00
[52] U.S. Cl. .................... 424/1; 424/1.5; 424/9; 562/433; 562/437; 562/441; 562/444; 562/449; 562/450
[58] Field of Search ............ 424/1, 1.5, 9; 562/433, 562/437, 441, 444, 449, 450

[56] References Cited

U.S. PATENT DOCUMENTS 4,017,596  4/1977  Loberg et al. ................... 424/1
4,091,088  5/1978  Hunt et al. ...................... 424/1

FOREIGN PATENT DOCUMENTS 2612698  3/1977  Fed. Rep. of Germany ......... 424/1
2723605  12/1977  Fed. Rep. of Germany ......... 424/1
2913173  10/1979  Fed. Rep. of Germany ......... 424/1
1545427  5/1979  United Kingdom ................. 424/1
2018762  10/1979  United Kingdom ................. 424/1

OTHER PUBLICATIONS

Burns et al., Chemical Abstracts, vol. 90, Feb. 1979, Abstract #71881g.
Fonda et al., Chemical Abstracts, vol. 89, 1978, Abstract #38806t.
Noronha et al., Chemical Abstracts, vol. 87, 1977, Abstract #179933c.
van Wyck et al., Eur. J. Nuc. Med. 4, 445–448, (1979).

*Primary Examiner*—Christine M. Nucker
*Attorney, Agent, or Firm*—Curtis, Morris & Safford

[57] ABSTRACT

What are disclosed are a diagnostic agent for visualizing the hepatobiliary system which agent contains Technetium-99m-labelled (2,4,5-trimethylacetanilido)-iminodiacetate in a suitable solvent, and a process for the preparation of this diagnostic agent; chloroacetic acid-(2,4,5-trimethylanilide) as an intermediate product and a process for the preparation thereof; and (2,4,5-trimethylacetanilido)-iminodiacetate and a process for the preparation thereof.

15 Claims, No Drawings

TECHNETIUM-99m-LABELLED (2,4,5-TRIMETHYLACETANILIDO)-IMINODIACETATE FOR LIVER FUNCTION DIAGNOSIS, CHLOROACETRIC ACID (2,4,5-TRIMETHYLANILIDE), (2,4,5-TRIMETHYLACETANILIDO)-IMINODIACETATE, AND PROCESS FOR THEIR PREPARATION

The present invention relates to a product for the scintigraphic visualization of the hapatobiliary system (liver, gallbladder, intra- and extra-hepatic biliary tract). The product is especially suitable for dynamic examinations.

Technetium-99m has prevailed lately in nuclear-medical diagnosis because of its favorable physical parameters (no corpuscular radiation, gamma-radiation energy of 140 keV, half-life of 6 hours) and thus low radiation stress for patients and personnel, and because of its simple preparation by means of nuclide generators.

Technettum-99m obtained from such generators is first present in the form of pertechnetate, and it is suitable in this form for scintigraphy of the thyroid gland and the brain. In order to make feasible a Tc-99m diagnosis of other organs, too, organospecific vehicular substances have been developed which can be easily labelled with Tc-99m and thus enable a good scintigraphic visualization of most different organs. For example, the RES-containing organs such as the liver and spleen are well visualized by means of labelled colloids; by certain labelled phosphorus compounds are suitable for bone scintigraphy, and so on.

For providing the vehicular substance with a Tc-99m label, the very slow-reacting pertechnetate ($TcO_4^-$) is first reduced to a lower oxidation level. In this form, technetium is reactive and forms a relatively stable complex with the corresponding vehicular substance.

$TcO_4^-$ can be reduced by chemical reducing agents or by electrolysis; however reduction by means of tin-(II) salts is preferred nowadays.

Reduction with tin(II) is advantageous in that the reducing agent and the organo-specific vehicular substance-generally in freeze-dried form—can be stored together in a vial, so that in the hospital only the generator eluate containing the $^{99m}Tc$ pertechnetate has to be added in order to obtain the ready-to-use product.

Because of the detectors available, nuclear-medical diagnosis, was limited for a long time to the localization of defined organs and the detection of alterations therein. Because in improvements of the gamma-camera and its coupling with electronic data processing systems, it has become possible to picture scintigrams in intervals of seconds and to record them. Such scintigram sequences not only permit visualization of a particular organ, for example the liver, but also permit diagnoses of the function thereof. Hence the term "function scintigraphy".

In a first stage, I-131-labelled substances capable of passing through the liver, such as $^{131}I$-rose bengal or $^{131}$iodobromosulfaleine have been used for liver function examinations. Because of the relatively high radiation dose and the relatively slow passage of these compounds through the liver, which is disadvantageous with respect to examination purposes, attempts were then made to find a diagnostic agent, capable of being Technetium-99m labelled for these examinations, which passes through the liver more rapidly.

According to the literature, mainly three different substances or classes of substances have been proposed for these examinations:
1. $^{99m}Tc$-Penicillamine (,e.g. G. T. Krishnamurathy et al., J. Nucl. Med. 13, 447 (1972);
2. $^{99m}$-Tc-Pyridoxalamino acids, especially $^{99m}Tc$-pyridoxalglutamate, e.g. R. J. Baker et al.; P. M. Ronai: J. Nucl. Med. 16, 720 (1975); and
3. $^{99m}Tc$-Acetanilido-iminodiacetate (e.g. E. Harvey et al. J. Nucl. Med. 16, 533 (1975).

Thus, $^{99m}Tc$-(2,6-dimethylacetanilido)-iminodiacetate (HIDA) and $^{99m}Tc$-(2,6-diethylacetanilido)-iminodiacetate (EHIDA) were used.

In British Patent Specification No. 1,545,427, compounds of the formula

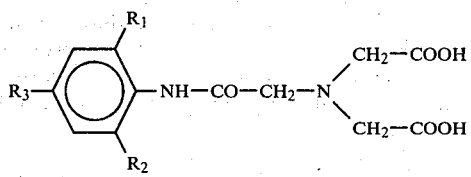

are described "in which at least two of the symbols $R_1$, $R_2$ and $R_3$ are lower alkyl groups having from 1 to 4 carbon atoms, the third is a hydrogen atom or a lower alkyl group having from 1 to 4 carbon atoms, and the three symbols represent in total at least three carbon atoms". Verbatim, (2,6-diethylacetanilido)-iminodiacetate, (2,6-diisopropylacetanilido)-iminodiacetate and (2,4,6-trimethylacetanilido)iminodiacetate are mentioned.

A certain amount of all of the derivatives of acetanilidoiminodiacetate hitherto described is excreted via the kidney, so that the kidney, too, is distinctly visualized.

The present invention provides a diagnostic agent for liver function diagnosis which is excreted via the kidney to an insignificant extent only and passes extremely rapidly through the liver, thus reducing examination time as much as possible.

The present invention further relates to a method for preparing a diagnostic agent for liver function diagnosis, which method comprises mixing (2,4,5-trimethylacetanilido)-iminodiacetate (TMIDA) in aqueous solution with a tin(II) salt in a molar ratio from 10:1 to 200:1, adjusting the solution to a pH from 4 to 9, preferably 5.0 to 6.5, and subsequently adding from 0.1 to 100 mCi, depending on the intended use, of Tc-99m pertechnetate in a suitable solvent, preferably in a physiological saline solution. The concentration of TMIDA and tin(II) salt, respectively, is advantageously from 0.1 to 200 mg/ml, and 0.01 to 5 mg/ml, respectively, preferably from 10 to 50 mg/ml and 0.1 to 0.5 mg/ml, respectively.

For preparing the diagnostic agent, it is advantageous to dissolve the (2,4,5-trimethylacetanilido)-iminodiacetic acid in water with addition of aqueous sodium hydroxide solution. NaOH is added in an amount required for the complete dissolution of the compound. The pH after this dissolution is from 7 to 10; the pH is then adjusted to about 5 with HCl. Subsequently, the corresponding amount of Sn(II) salt (dissolved in 0.1 N HCl) is added, the batch is agitated for 30 minutes under a protective gas atmosphere, and the pH is adjusted to 6.

The tin (II) salt employed may be $SnCl_2 \cdot 2H_2O$, $SnF_2$, $SnSO_4$, Sn tartrate, SnO, Sn oxalate, Sn acetate, or another tin (II) salt.

By adding Technetium-99m pertechnetate, this solution can be applied within 24 hours as ready-to-use diagnostic agent. On the other hand, it may be frozen or lyophilized for storage purposes. The lyophilized product is stable for at least 8 months under a protective nitrogen atmosphere.

The present invention further relates to a diagnostic agent for visualizing the hepatobiliary system, which agent comprises Technetium-$99m$ labelled (2,4,5-trimethylacetanilido)iminodiacetate in a suitable solvent, preferably a physiological saline solution.

The diagnostic agent is preferably administered intravenously in a physiological saline solution in a dose from 0.04 to 0.4 mg/kg of body weight. One labelling unit advantageously contains 30 mg. As compared to the hitherto known products, the novel diagnostic agent is distinguished by a more rapid passage through the liver and a decreased activity concentration in the kidney, which advantages are demonstrated in the following animal tests:

(1) 0.5 mCi of the labelled diagnostic agent ia administered to a rabbit by injection into the ear vein, and the distribution of the activity is observed during the passage of time by means of a gamma-camera connected with a data processing system. The progress of the activity in defined organs is thus observed. The following parameters are determined:

1. liver$_{max}$=time of maximal liver activity after the injection
2. liver$_{max/2}$=half-life of the activity in the liver (outside of the gallbladder).

The data for some derivatives of acetanilido-iminodiacetate are listed in the following Table 1:

| Substitution in the aromatic compound | | liver$_{max}$ | liver$_{max/2}$ |
|---|---|---|---|
| 2,6-dimethyl- | (HIDA) | 5.7 min. | 8.2 min. |
| 2,6-diethyl- | (EHIDA) | 6.8 min. | 15.7 min. |
| 2,6-diisopropyl- | | 4.6 min. | 15.3 min. |
| 2,4,6-trimethyl | | 4.2 min. | 10.0 min. |
| 2,4,5-trimethyl- | (TMIDA) | 2.6 min. | 7.7 min. |

2. 30 μCi each of the labelled diagnostic agent are administered to groups of 12 rats each by injection into the thigh vein. Subsequently, 3 animals each are killed after 5, 10, 20 and 30 minutes, and the distribution of radioactivity in the organs is determined. The results are listed in the following Table 2:

| Substitution in the aromatic compound | | time | liver | intestines | kidneys |
|---|---|---|---|---|---|
| 2,6-dimethyl- | (HIDA) | 5' | 21.7% | 43.2% | 7.4% |
| | | 10' | 9.6% | 65.9% | 7.4% |
| | | 20' | 2.2% | 80.8% | 5.8% |
| | | 30' | 1.0% | 79.7% | 4.9% |
| 2,6-diethyl- | (EHIDA) | 5' | 6.9% | 71.2% | 4.3% |
| | | 10' | 3.4% | 79.9% | 4.2% |
| | | 20' | 1.6% | 81.7% | 3.6% |
| | | 30' | 1.5% | 81.8% | 3.4% |
| 2,6-diisopropyl- | | 5' | 10.0% | 60.9% | 4.4% |
| | | 10' | 7.0% | 65.3% | 4.4% |
| | | 20' | 4.4% | 71.9% | 4.4% |
| | | 30' | 4.4% | 72.2% | 3.8% |
| 2,4,6-trimethyl- | | 5' | 23.5% | 57.0% | 3.6% |
| | | 10' | 12.1% | 66.0% | 3.8% |
| | | 20' | 2.9% | 79.2% | 3.8% |
| | | 30' | 1.6% | 81.0% | 3.3% |
| 2,4,5-trimethyl- | (TMIDA) | 5' | 19.1% | 56.8% | 3.3% |
| | | 10' | 9.6% | 68.8% | 3.1% |
| | | 20' | 2.4% | 81.1% | 2.5% |
| | | 30' | 1.2% | 82.0% | 2.1% |

The dosis tolerata maxima of the diagnostic agent is 189 mg/kg of body weight in the case of mice and rats; the LD$_{50}$ per kg of test animal is 246 mg in mice and 255 mg in rats.

The present invention further relates to chloracetic acid (2,4,5-trimethylanilide) and a method for the preparation thereof, which method comprises reacting 2,4,5-trimethylaniline with chloroacetic acid chloride.

The present invention also relates to (2,4,5-trimethylacetanilido)-iminodiacetate and a method for the preparation thereof, which method comprises reacting chloroacetic-acid-(2,4,5-trimethylanilide) in an alkaline medium with iminodiacetic acid.

The following examples illustrate the invention.

EXAMPLE 1

Preparation of (2,4,5-trimethylacetanilido)-iminodiacetate

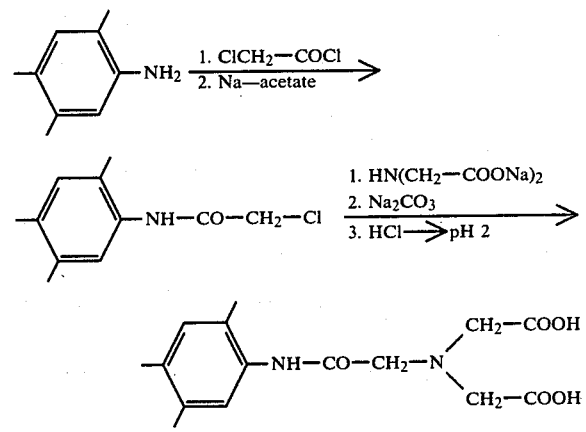

(a) 13.52 g (0.1 mol) of 2,4,5-trimethylaniline are dissolved in 80 ml of glacial acetic acid. The solution is cooled to 10° C., 12.4 g (0.11 mol) of chloroacetic acid chloride are added, and the batch is thoroughly intermixed. Subsequently, 100 ml of semi-saturated aqueous sodium acetate solution and 100 ml of water are added with thorough agitation and agitation is continued for a further 30 minutes. The chloroacetic acid-(2,4,5-trimethylanilide) precipitated is suction-filtered and recrystallized from methanol.

melting point: 163°–165° C.

| Elementary analysis: | C | H | N | Cl |
|---|---|---|---|---|
| calc. | 62.41% | 6.67% | 6.62% | 16.75% |
| found | 62.5% | 6.6% | 6.7% | 16.8% |

NMR (in DMSO—d$_6$, internal standard: TMS):
—CH$_2$—: δ = 4.23 ppm(s)
—NH—: δ = 9.48 ppm(s)
arom.: 3-H: δ = 6.94 ppm(s)
6-H: δ = 7.09 ppm(s)
2-CH$_3$: δ = 2.10 ppm(s)

-continued

| 4-CH$_3$: | $\delta$ = 2.15 ppm(s) |
| 5-CH$_3$: | $\delta$ = 2.15 ppm(s) |

(b) 4.0 g (22 mmols) of iminodiacetic acid disodium salt, 5.7 g (20 mmols) of Na$_2$SO$_3$.10H$_2$O and 4.25 g (20 mmols) of chloroacetic acid-(2,4,5-trimethylanilide) are added to 100 ml of water and 100 ml of ethanol and the batch is refluxed for 24 hours. After cooling, the solvent is removed and the residue is dissolved in about 150 ml of water. This aqueous solution is washed 4 times with about 50 ml of diethylether and, subsequently, the pH is slowly brought to 2 with HCl. The precipitated product is suction-filtered, again dissolved in water with addition of that amount of NaOH required to dissolve the substance completely. After filtration, (2,4,5-trimethylacetanilido)-iminodiacetic acid is precipitated again by adding HCl until the pH is adjusted at 2, suction-filtered and dried.

melting point: 196°–198° C.

| Elementary analysis: | C | H | N |
|---|---|---|---|
| calc. | 58.43% | 6.54% | 9.09% |
| found | 58.3% | 6.6% | 9.0% |

NMR (in DMSO—d$_6$, int. standard: TMS):

$>$N—CH$_2$—COOH: $\delta$ = 3.55 ppm(s)

—CO—CH$_2$—N$<$ : $\delta$ = 3.42 ppm(s)

—NH—: $\delta$ = 9.49 ppm(s)
—COOH: $\delta$ = 12.5 ppm(s)
arom.: 3-H: $\delta$ = 6.94 ppm(s)
6-H: $\delta$ = 7.56 ppm(s)
2-,4-,5-CH$_3$: $\delta$ = 2.15 ppm(s)

EXAMPLE 2

1.8 g (2,4,5-trimethylacetanilido)-iminodiacetic acid is dissolved in 20 ml of 0.5 N sodium hydroxide solution and 36 mg of SnCl$_2$.2H$_2$O (dissolved in 6 ml of 0.1 N hydrochloric acid) are added. The batch is stirred for 5 minutes, the pH is adjusted to 6 by means of hydrochloric acid, the batch is brought to 60 ml and divided into 1 ml portions. 10 mCi of Tc-99m pertechnetate in 4 ml of physiological saline solution are added to such a portion. After 30 minutes, 0.5 ml of the diagnostic agent so prepared is administered intravenously to a rabbit (some data of this test are indicated in Table 1). All operations were carried out under a protective N$_2$ gas atmosphere.

EXAMPLE 3

7 g of (2,4,5-trimethylacetanilido)-iminodiacetic acid are dissolved in 100 ml of 1 N sodium hydroxide solution and 16.5 mg of SnF$_2$ (dissolved in 5 ml of 0.1 N hydrochloric acid) are added. After stirring for 5 minutes, the pH is adjusted to 6 by means of hydrochloric acid, the batch is brought to 233 ml, divided into 1 ml portions in beaded rim vials, and frozen with liquid nitrogen. Subsequently, the product is lyophilized, the vials are filled with nitrogen and closed. After a storage time of 60 days, 0.3 mCi to Tc-99m pertechnetate in 10 ml of physiological saline solution is injected into the closed vials. After a reaction time of 20 minutes, 0.5 ml each of the diagnostic agent so obtained is administered intravenously to rats (typical test results are indicated in Table 2).

We claim:

1. A method for making (2,4,5-trimethylacetanilido)iminodiacetate which comprises reacting N-(2,4,5-trimethylphenyl)chloroacetamide with iminodiacetic acid in an alkaline medium.

2. (2,4,5-trimethylacetanilido)-iminodiacetate.

3. N-(2,4,5-trimethylphenyl)-chloroacetamide.

4. A method for making N-(2,4,5-trimethylphenyl)-chloroacetamide which comprises reacting 2,4,5-trimethylaniline with chloroacetic acid.

5. A diagnostic agent for visualizing the hepatobiliary system, which agent comprises a scintigraphically-detectable amount of (2,4,5-trimethylacetanilido)-iminodiacetate, labelled with Technetium-99m, in an injectable solvent therefor.

6. A diagnostic agent as in claim 5 wherein said solvent is physiological saline solution.

7. A method for making a diagnostic agent for liver function diagnosis, which method comprises mixing (2,4,5-trimethylacetanilido)-iminodiacetate and a salt of tin (II) in water in a molar ratio from 10:1 to 200:1 to form an aqueous solution, adjusting the solution to a pH from 4 to 9, and then adding thereto fron 0.1 to 100 mCi of Tc-99m pertechnetate in a solvent therefor.

8. A method as in claim 7 wherein the concentration of said iminodiacetate in said diagnostic agent is from 0.1 to 200 mg/ml.

9. A method as in claim 7 wherein the concentration of said iminodiacetate in said diagnostic agent is from 10 to 50 mg/ml.

10. A method as in claim 7 wherein said salt of tin (II) is a member selected from the group consisting of SnCl$_2$.2H$_2$O, SnF$_2$, SnSO$_4$, SnO, Sn tartrate, Sn oxalate, and Sn acetate.

11. A method as in claim 7 wherein, prior to the addition of Tc-99m pertechnetate thereto, said aqueous solution of (2,4,5-trimethylacetanilido)-iminodiacetate and said salt of tin (II) is divided into small portions and said small portions are lyophilized, whereby each said small lyophilized portion becomes a labelling unit adaptable to separate labelling by the addition of Tc-99m pertechnetate thereto.

12. A method as in claim 11 wherein the solvent for said Tc-99m pertechnetate is physiological saline solution.

13. A method as in claim 11 wherein a small portion contains from 1 to 200 mg of said iminodiacetate and from 0.01 to 5 mg of said salt of tin (II).

14. A method as in claim 11 wherein a small portion contains from 10 to 50 mg of said iminodiacetate and from 0.1 to 0.5 mg of said salt of tin (II).

15. A method for visualizing the hepatobiliary system of a patient which comprises intravenously administering to said patient a scintigraphically-detectable amount of (2,4,5-trimethylacetanilido)-iminodiacetate, labelled with Technetium-99m, and detecting the same in the hepatobiliary system of said patient by scintigraphy.

* * * * *